United States Patent

Fofonoff et al.

[11] Patent Number: 5,911,942
[45] Date of Patent: *Jun. 15, 1999

[54] METHOD FOR SPINNING AND PROCESSING COLLAGEN FIBER

[75] Inventors: Timothy W. Fofonoff, Dedham; Eugene Bell, Boston, both of Mass.

[73] Assignee: Tissue Engineering, Inc., Boston, Mass.

[*] Notice: This patent is subject to a terminal disclaimer.

[21] Appl. No.: 08/817,446

[22] PCT Filed: Nov. 2, 1995

[86] PCT No.: PCT/US95/14188

§ 371 Date: May 1, 1997

§ 102(e) Date: May 1, 1997

[87] PCT Pub. No.: WO96/14452

PCT Pub. Date: May 17, 1996

[51] Int. Cl.$^6$ .............. B05D 1/04; B05D 3/12; D01F 4/00
[52] U.S. Cl. .............. 264/444; 28/220; 264/85; 264/131; 264/202; 264/210.3; 264/210.8; 264/211.15; 427/174; 427/175; 427/180; 427/434.6; 427/601
[58] Field of Search .............. 264/85, 131, 202, 264/210.3, 210.8, 211.15, 444; 425/66, 68, 71, 93, 174.2, 377, 382.2, 461, 464; 427/174, 175, 180, 434.6, 601; 118/33, 420, 423, 428, 612, DIG. 18, DIG. 19; 28/220, 240

[56] References Cited

U.S. PATENT DOCUMENTS

| | | | |
|---|---|---|---|
| 2,485,958 | 10/1949 | Cresswell | 264/202 |
| 2,581,938 | 1/1952 | Swanson et al. | 118/420 |
| 2,637,321 | 5/1953 | Cresswell | 264/202 X |
| 2,723,900 | 11/1955 | Hooper | 18/54 |
| 2,748,774 | 6/1956 | Novak | 128/335.5 |
| 2,892,675 | 6/1959 | Bradshaw | 8/151 |
| 2,962,766 | 12/1960 | Hinkle et al. | 18/57 |
| 3,121,762 | 2/1964 | Hafstad et al. | 264/99 |
| 3,139,467 | 6/1964 | Drisch et al. | 264/198 |
| 3,147,144 | 9/1964 | Wilhelm | 118/420 |
| 3,272,204 | 9/1966 | Artandi et al. | 128/334 |
| 3,453,194 | 7/1969 | Bennett et al. | 204/159.12 |
| 4,144,079 | 3/1979 | Smith | 106/164 |
| 4,148,664 | 4/1979 | Cruz, Jr. | 106/161 |
| 4,215,200 | 7/1980 | Miyata et al. | 435/273 |
| 4,485,096 | 11/1984 | Bell | 424/95 |
| 4,485,097 | 11/1984 | Bell | 424/95 |
| 4,501,815 | 2/1985 | Reid et al. | 435/284 |
| 4,505,266 | 3/1985 | Yannas et al. | 128/1 R |
| 4,642,292 | 2/1987 | Reid et al. | 435/240 |

(List continued on next page.)

FOREIGN PATENT DOCUMENTS

| | | |
|---|---|---|
| 0 358 506 A3 | 3/1990 | European Pat. Off. |
| 1470662 | 4/1977 | United Kingdom . |
| 2063937 | 6/1981 | United Kingdom . |
| 2073620 | 10/1981 | United Kingdom . |
| WO94/3584 | 2/1994 | WIPO . |

OTHER PUBLICATIONS

Adams, J.C. and Watt, F.M., "Regulation of Development and Differentiation by the Extracellular Matrix," *Development*, 117:1183–1198 (1993).

Edgington, Stephen M., "3–D Biotech: Tissue Engineering," *Bio/Technology*, 10:855–860 (Aug. 1992).

Lin, C.Q. and Bissell, M.J., "Multi–faceted Regulation of Cell Differentiation by Extracellular Matrix," *The FASEB Journal*, 7:737–743 (Jun. 1993).

Nathan, C. and Sporn, M., "Cytokines in Context,"*Journal of Cell Biology*, 113:981–986 (1991).

Woessner, J. Frederick, Jr., Introduction to Serial Reviews: The Extracellular Matrix,: *The FASEB Journal*, 7:735–736 (Jun. 1993).

*Primary Examiner*—Leo B. Tentoni
*Attorney, Agent, or Firm*—Lahive & Cockfield, LLP

[57] ABSTRACT

An apparatus for forming a collagen fiber having microparticulates coated on the surface of the fiber and the method for forming the fiber are disclosed.

26 Claims, 2 Drawing Sheets

U.S. PATENT DOCUMENTS

| | | | |
|---|---|---|---|
| 4,645,669 | 2/1987 | Reid | 424/95 |
| 4,661,111 | 4/1987 | Ruoslahti et al. | 623/11 |
| 4,776,853 | 10/1988 | Klement et al. | 8/94.11 |
| 4,795,459 | 1/1989 | Jauregui | 623/1 |
| 4,801,299 | 1/1989 | Brendel et al. | 623/1 |
| 4,814,120 | 3/1989 | Huc et al. | 264/28 |
| 4,835,803 | 6/1989 | Mizushima | 8/128.1 |
| 4,837,285 | 6/1989 | Berg et al. | 530/356 |
| 4,871,500 | 10/1989 | Harms et al. | 264/178 R |
| 4,891,359 | 1/1990 | Saferstein et al. | 514/21 |
| 4,902,453 | 2/1990 | Okura et al. | 264/29.2 |
| 4,902,508 | 2/1990 | Badylak et al. | 424/95 |
| 4,935,000 | 6/1990 | Dudek | 600/36 |
| 4,956,178 | 9/1990 | Badylak et al. | 424/551 |
| 4,969,912 | 11/1990 | Kelman et al. | 623/66 |
| 4,981,841 | 1/1991 | Gibson | 514/2 |
| 4,983,580 | 1/1991 | Gibson | 514/2 |
| 5,007,916 | 4/1991 | Linsky et al. | 606/151 |
| 5,024,841 | 6/1991 | Chu et al. | 424/422 |
| 5,043,278 | 8/1991 | Nagaoka et al. | 435/181 |
| 5,043,426 | 8/1991 | Goldstein | 530/356 |
| 5,102,690 | 4/1992 | Iyer et al. | 427/57 |
| 5,110,604 | 5/1992 | Chu et al. | 424/484 |
| 5,192,312 | 3/1993 | Orton | 623/2 |
| 5,254,471 | 10/1993 | Mori et al. | 435/240.23 |
| 5,344,917 | 9/1994 | Furukawa et al. | 530/356 |
| 5,378,469 | 1/1995 | Kemp et al. | 424/423 |
| 5,562,946 | 10/1996 | Fofonoff et al. | 427/180 X |

METHOD FOR SPINNING AND PROCESSING COLLAGEN FIBER

BACKGROUND OF THE INVENTION

The use of synthetic materials, such as polyester fiber (Dacron™) or polytetrafluoroethylene (PTFE) (Teflon™), as implants designed to replace diseased or damaged body parts has been extensive. These materials have however, enjoyed limited success. This has been due to the poor biocompatibility of many of these materials which among other problems, frequently initiate persistent inflammatory reactions. Additionally, the failure of the body to integrate these materials, because they do not break down and do not lend themselves to remodeling by tissue cells that may come into contact with them, causes further problems.

Efforts to use animal or human materials have also been unsatisfactory when these materials are crosslinked by formaldehyde or glutaraldehyde, for example. The process of generalized aldehydic crosslinking renders biomaterials sufficiently unrecognizable to tissue cells so that normal remodeling and integration are not promoted. Similarly, other types of chemical processing of animal or human biomaterials, such as extraction with detergents, or hypertonic buffers or hypotonic buffers can alter them to the degree that they are ineffective in promoting angiogenesis and in stimulating repair and remodeling processes needed for the conversion of an implant into a functional substitute for the tissue or organ being replaced.

A third approach has been that of reconstituting tissue and organ equivalents from structural matrix components, such as collagen, for example, that have been extracted and purified and combined with specialized cells. The process depends upon interactions between the cells and matrix proteins that the cells condense and organize. While tissue-like constructs have been fabricated and been shown to somewhat resemble their natural counterparts, they do not readily develop the matrix complexity characteristic of the actual tissues they are meant to imitate.

Therefore, a need exists for an improved apparatus and method for spinning and processing collagen fibers which will enrich them with the other constituents of the extracellular matrix.

SUMMARY OF THE INVENTION

The invention relates to a method for forming a collagen fiber having microparticulates coated to the surface of the fiber. The method includes directing a liquid collagen solution into a coagulation bath to form a continuous collagen gel fiber. The continuous collagen gel fiber is removed from the coagulation bath and directed into dehydrating bath, whereby the collagen gel fiber is partly dehydrated undergoing further polymerization. The partially dehydrated collagen fiber is removed from the dehydrating bath. Microparticulates are coated to the surface of the fiber, and the fiber is stretched. The microparticulate-coated fiber is then further dried.

The present invention also relates to an apparatus for forming microparticulate-coated collagen fibers. The apparatus includes means for forming a continuous liquid collagen stream. The apparatus also includes a coagulation bath, wherein a continuous liquid collagen stream can form a continuous collagen gel fiber, and a dehydrating bath, wherein the continuous gel fiber can be partially dehydrated. Also included are means for applying microparticulates to the surface of the dehydrated fiber and means for stretching the microparticulate-coated fiber. The apparatus further has means for drying the microparticulate-coated fiber.

The present invention further includes an apparatus for applying microparticulates to the surface of a fiber. The apparatus includes a support base and a horizontal tube disposed on the support base. The tube has a first opening and a second opening, wherein the diameter of the tube is sufficient to allow passage of a continuous fiber under tension in a straight line into the first opening and from second opening. The apparatus also includes a microparticulate reservoir within the tube wherein the upper level of the reservoir is lower than the continuous fiber that can be drawn through the tube. The collagen fiber or yarn can be coated with microparticulates by forming a cloud of microparticulates in the tube, wherein the microparticulates can contact the fiber and be applied to the surface of the fiber. In a preferred embodiment, the horizontal tube is an inverted arch, wherein the lower portion of the tube forms the microparticulate reservoir.

The present invention has many advantages. The method and apparatus allows the formation of a uniform collagen fiber with finely coated microparticulates. Further, the method and apparatus allow coating of the collagen fiber without wasting the microparticulates since the excess falls continuously into the reservoir.

DETAILED DESCRIPTION OF THE INVENTION

The features and other details of the method and apparatus of the invention will now be more particularly described with reference to the accompanying drawings and pointed out in the claims. The same numeral present in different figures represents the same item. It will be understood that the particular embodiments of the invention are shown by way of illustration and not as limitations of the invention. The principal features of this invention can be employed in various embodiments without departing from the scope of the invention. All parts and percentages are by weight unless otherwise specified.

Figure 1:
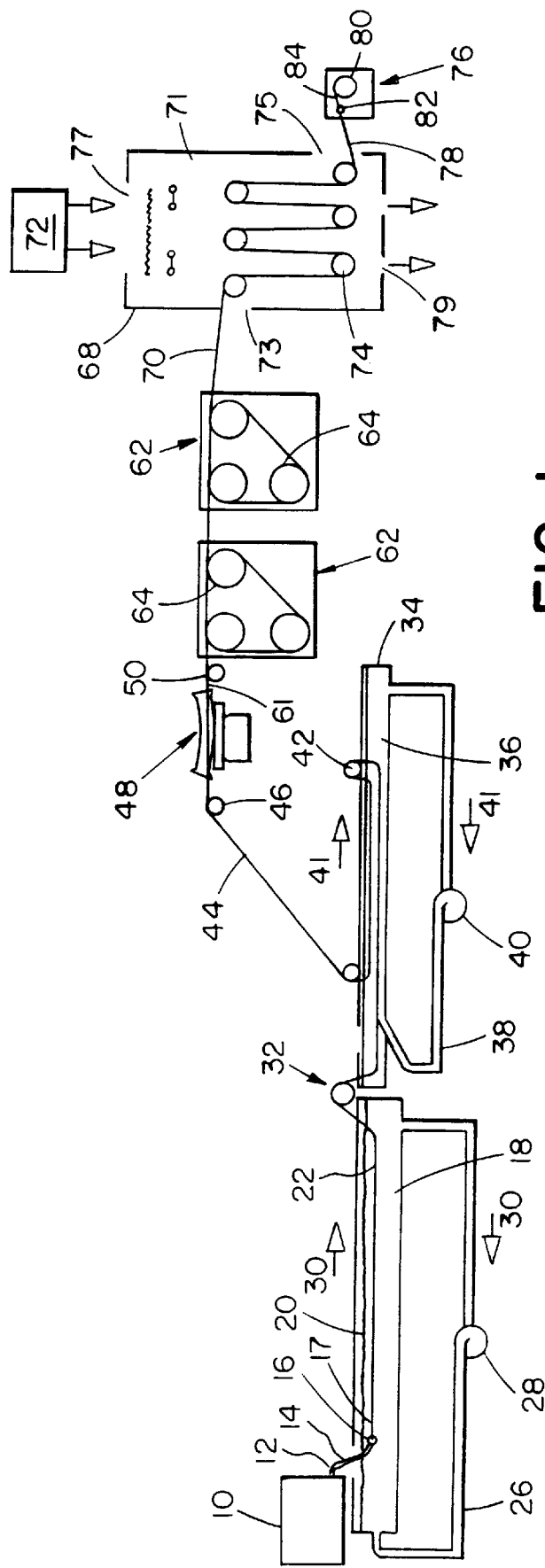
FIG. 1 is a schematic diagram of an apparatus of the present invention for forming a collagen fiber having microparticulates coated on the surface of the fiber.

One embodiment of the invention, as shown in FIG. 1 in a schematic view, is an apparatus for forming a collagen fiber having microparticulates coated on the surface of the fiber. The apparatus has collagen reservoir chamber 10 which is for holding a liquid collagen solution. The collagen can be derived from a suitable animal source, such as porcine, bovine, ovine or marine animal extracellular matrix from many tissues such as dermis, tendons, dental and connective tissue as well as others. In one embodiment, a suitable chamber is a stainless steel syringe. Reservoir tube 12 is attached to collagen reservoir chamber 10 for directing collagen solution from collagen reservoir chamber 10 through infusion pump 14 to spinneret 16. Infusion pump 14 is capable of raising the pressure of the collagen material such that it can be extruded through spinneret nozzle 17 of spinneret 16. In a preferred embodiment, a positive displacement metering pump is used. Spinneret 16 can be single bore or multiple bore to produce monofilament or multifilament fibers respectively. The spinneret bores can be of various diameters or have tapered profiles to form fibers of different sizes and tensile strengths. Co-component fibers can be produced with other specialized spinnerets as are known in the art. In one embodiment, spinneret nozzle 17 has diameters in the range of between about 100 and 1,000 microns.

Coagulation bath 18 has a coagulation solution 20 that can cause the liquid collagen to form a collagen gel, such as a 0.75% alkaline alginic acid in a boric acid buffer or sugar solutions or polyethylene glycol solution which also has hydrophilic properties. The opening of spinneret is immersed in a flowing coagulation solution 20. Coagulation bath 18 is suitably sized for allowing extrusion of fiber from spinneret 16 through coagulation solution 20 while having a sufficient residency time for collagen gel fiber 22 to form. Coagulation bath 18 can be heated and instrumented for monitoring the relevant process variables, such as temperature, pH and velocity. Coagulation bath 18 allows collagen gel 22 fiber to be formed in a horizontal trough or in a tube or vertically in a tube. Coagulation bath 18 is configured to allow circulation of coagulation solution 20 through recirculating loop 26 by circulating pump 28. Coagulation bath flow can be in the same direction 30 of fiber travel. At the end of the coagulation bath 18, roller 32 is for directing fiber out of the coagulation bath. Roller 32 is motorized and can be activated to wind collagen gel fiber 22 and subsequently tow collagen gel fiber 22 at desired speeds.

Dehydrating bath 34 is adjacent to roller 32 and coagulation bath 18 and is configured to allow fiber 22 to be drawn into dehydrating bath 34 from roller 32. Dehydrating bath 34 holds dehydrating solution 36, such as 90% ethanol, which allows further dehydration and annealing of the fiber and promotes polymerization of the collagen to improve fiber strength. An example of another suitable dehydration solution composition is acetone. Dehydrating bath 34 is configured to allow variable circulation of dehydrating solution 36 through recirculating loop 38 by circulating pump 40 which can be adjusted directionally, such as direction 41 or in the opposite direction. Return rollers 42, which can be near each end of dehydrating bath 34, allow the fiber path to be lengthened by doubling back to make any number of multiple passes through dehydrating bath 34 to allow further dehydration and promote polymerization of the collagen.

Partially dehydrated fiber 44 is wound around first applicator roller 46, through particulate applicator 48 to second applicator roller 50. Particulate applicator 48 applies a coating of microparticulates to the surface of a fiber as it passes through the applicator. Particulate applicator 48 allows the use of very small powder volumes of high value microparticulates, such as animal derived matrix (ADMAT), to be coated on the fiber with precision and control and with little loss of particulate matter as waste. Particulate applicator 48 can be operated intermittently as the fiber is passed through the application chamber to allow alternatively coated and uncoated sections of fibers. Particulate applicator 48 can provide a fiber drying effect via the hydration of the contacting dehydrated microparticulates by drawing liquid from the fiber, thereby aiding fiber polymerization. In a preferred embodiment, particulate applicator 48 has tube 52 curved in an inverted arch.

Figure 2:
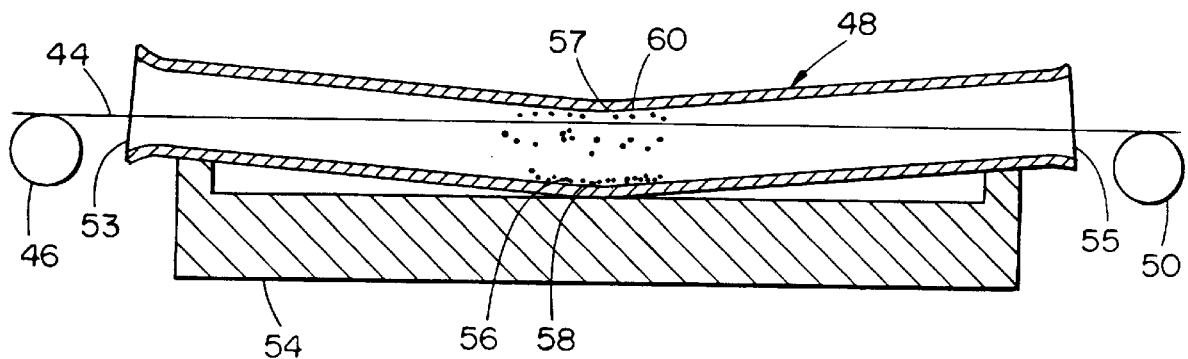
FIG. 2 is a cross-sectional view of an apparatus for coating microparticulates on the surface of a fiber.
Figure 3:
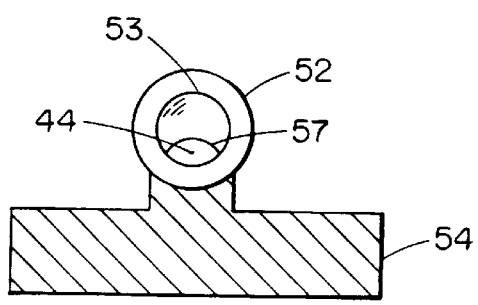
FIG. 3 is an end view of the apparatus shown in FIG. 2.

As shown in a cross-sectional view in FIG. 2 and in an end view in FIG. 3, lower portion 58 of tube 52, which is attached to support base 54, forms particulate reservoir 56. Tube 52 has a first opening 53 for receiving fiber 44 and second opening 55 at the other end of tube 52 to allow passage of fiber 44 under tension in a straight line to second applicator rollers 50. Particulate applicator 48 has a pathway which is straight that is achieved by limiting the bend angle at upper portion 60 of the tube 52 such that the apex 57 of the top interior wall of chamber formed within the tube does not project below a height above first opening 53 and second opening 55 of tube 57.

In base 54, particle applicator 48 has means for suspending microparticulate particles to produce a particle cloud within tube 52. The vibrational energy used to produce the cloud can be varied. Tube 52 is sufficiently sized to accommodate the maximum horizontal displacement amplitude of the input vibration, plus the diameter of the fiber. The vibrational frequency can be in the range of between about 1,000 and 3,000 cycles per minute for the size chamber used. The density of the dust cloud can be varied by changing the microparticulate mass and the frequency of vibration. Tube 52 is attached to a vibration means capable of producing the requisite horizontal and vertical components of vibration. The vibration can excite the microparticulates into motion to produce a dust cloud of a density dependent upon the amplitude and frequency of the vibration.

Tube 52 is sufficiently sized to allow airborne microparticulates which do not adhere to the fiber to settle into particulate reservoir pool 56 either directly or by sliding down the entrance or exit ramp floors of particulate applicator 48. Such microparticulates can be recycled back into microparticulate dust cloud within particulate applicator 48. In one embodiment, tube 52 has a diameter of about 1.8 cm, a length of about 17 cm and a bend angle of about 150°.

Returning to FIG. 1, stretching roller means 62 is for receiving fiber from particulate applicator 48, wherein the fiber can undergo a controlled deformation by being stretched between two groups of rollers 64 rotating at slightly different rates of speed. The speed of rotation of rollers 64 can be precisely controlled with digital microprocessors arranged in a closed feedback loop. The fibers are wrapped around each roller 64 several times to prevent fiber slippage relative to the roller surfaces. Roller 64 surfaces can made of a polymer or a hardened metal resistant to corrosion. Roller 64 rotations can be adjusted individually to allow the fiber to be stretched beyond the elastic yield point to produce a longer fiber of reduced diameter. Stretching roller means 62 can operate under semi-dry or dry conditions and also under high moisture content atmosphere.

Drying cabinet 68 has opening 73 for receiving stretched fiber 70 from stretching rollers 62. Drying cabinet 68 has passage 71 through drying cabinet 68 for receiving warm, dry filtered air or a dry inert gas, such as dry nitrogen gas, from gas source 72 at a suitable temperature and humidity for drying stretched fiber 70. The air can be passed through air passage opening 77 into passage 71 and exiting from air passage opening 79. In one embodiment, the temperature of the air is between about 35° C. and 39° C. The humidity is in the range of between 10 and 20 percent relative humidity. Drying cabinet 68 has a series of rollers 74 which allows stretched fiber 70 to remain in drying cabinet 68 while being rolled, thereby increasing the residence time of fiber 70 in drying cabinet 68. Drying cabinet rollers 74 are adjustable in distance between each other and to compensate for the fiber line speed. Drying cabinet rollers 74 can be driven at a surface roller speed that can be synchronized with that of stretching roller means 62. Drying cabinet 68 has a door to provide access to the rollers for threading the leader thread.

Take-up winder 76 is for receiving dried fiber 78 from exit 75 of drying cabinet 68. Take-up winder 76 has spool 80 for receiving dried fiber on a removable spindle bobbin. Take-up winder 76 has a slip clutch 82 to provide a constant fiber line tension and fiber line speed as the spooled fiber rotates radially around spool 80. Fiber spool 80 can wind the fiber level or by randomly winding with the take-up winder 76.

A preferred source material for a source of collagen consists of the skins from near-term, domestic porcine fetuses which are harvested intact, enclosed in their amniotic membranes. Embryonic and fetal tissues are advantageous because they include various molecular factors which are present in normal tissue at different stages of animal development. Other sources for extracellular matrix material are diverse tissues found in organs from porcine, bovine, ovine, marine or other animals.

The collagen fibers or yarn decorated with the informational microparticulates can be used to create strips, sheets, tubes and other shapes using textile machinery by those skilled in the art. The shapes can be in the form of tissues or body parts to be replaced and constitute prostheses.

The extracellular matrix particulates taken from specific tissues have two kinds of informational properties. The first is their molecular diversity and the second is their microarchitecture both preserved in the preparation of the microparticulates. The preferred associations among the different molecules of the extracellular matrix are also preserved in the preparation of the microparticulates.

The extracellular matrix particulates can have cytokines, including growth factors necessary for tissue development. These biomolecular factors are present in normal tissue at different stages of tissue development, such as cell division morphogenesis and differentiation. Among these factors are stimulatory molecules that provide the signals needed for in vivo tissue repair. These cytokines including growth factors, being part of the extracellular matrix microparticulates, can stimulate conversion of an implant into a functional substitute for the tissue being replaced. It is believed that it can do this by mobilizing tissue cell from contiguous like tissues, from the circulation and from stem cell reservoirs; it can promote cell division, morphogenesis and differentiation. Cells can attach to the prostheses which are bioabsorbable and can remodel them into replacement tissues.

Growth factors necessary for cell growth are attached to structural elements of the extracellular matrix. The structural elements include proteins, glycoproteins, proteoglycans and glycosaminoglycans. The growth factors, originally produced and secreted by cells, bind to the extracellular matrix and regulate cell behavior in a number of ways. These factors include, but are not limited to, epidermal growth factor, fibroblast growth factor (basic and acidic), insulin growth factor, nerve growth-factor, mast cell-stimulating factor, platelet-derived growth factor, the family of transforming growth factor-β, platelet-derived growth factor, scatter factor, hepatocyte growth factor and Schwann cell growth factor. Adams et al., "Regulation of Development and Differentiation by the Extracellular Matrix" *Development* Vol. 117, p. 1183–1198 (1993) (hereinafter "Adams et al.") and Kreis et al. editors of the book entitled "Guidebook to the Extracellular Matrix and Adhesion Proteins," Oxford University Press (1993) (hereinafter "Kreis et al.") provide contributions which summarize extracellular matrix components that regulate differentiation and development and describe the regulatory mechanisms involved and that growth factors and extracellular matrix molecules interact in a number of ways to regulate cell behavior. Further, Adams et al. disclose examples of association of growth factors with extracellular matrix proteins and that the extracellular matrix is an important part of the micro-environment and, in collaboration with growth factors, plays a central role in regulating differentiation and development. The teachings of Adams et al. and Kreis et al. are incorporated herein by reference.

The method for forming extracellular matrix microparticulates for producing graft tissue includes freezing a tissue source having living cells, whereby the living cells are disrupted to form cell remnants. The tissue source is then cryomilled to produce microparticulates which are thawed and are processed leaving extracellular matrix microparticulates including cytokines. The term cytokines includes but is not limited to growth factors, interleukins, interferons and colony stimulating factors. The process of washing removes the cell remnants without removing growth and other factors necessary for cell growth, morphogenesis and differentiation. The extracellular matrix is freeze-dried and, if desired, further fragmented.

A method for forming extracellular matrix microparticulates for producing graft tissue is disclosed in U.S. patent application Ser. No. 07/926,885, filed Aug. 7, 1992, entitled "A Method for Producing Graft Tissue Extracellular Matrix". The teachings of which are herein incorporated by reference. The method for forming extracellular matrix microparticulates for producing graft tissue includes freezing a connective tissue source having living cells, whereby the living cells are disrupted to form cell remnants. The connective tissue source is processed to remove the cell remnants without removing growth factors necessary for cell growth, differentiation, and morphogenesis to form an extracellular matrix. The extracellular matrix is freeze-dried and fragmented. The extracellular matrix is further processed to remove cytoplasmic and nuclear components without removing the growth factors necessary for cell growth to form extracellular matrix microparticulates. In one embodiment, the extracellular matrix particulates associated with collagen fibers in a three-dimensional matrix are exposed to cultivated cells under such conditions that the cultivated cells adhere to the extracellular matrix microparticulates, alone or to the microparticulates and the collagen fibers thereby producing graft tissue.

In a preferred method for extracting the collagen from tissue, a collagen source includes porcine fetuses. The fetuses are frozen in utero with the uteri maintained in an unbroken condition with the ends tied off by string. Twelve to twenty-four hours before dissection, a uterus is removed from the freezer and placed in a 4° C. cold room. The uterus, which should still be about 90% frozen, is transferred into a large sterile dishpan. As soon as possible, the folded uterus is gently straightened. The exterior surface of the uterus is washed twice for 10 minutes in 1% bleach in Milli-Q™ water and is then washed twice with sterile Milli-Q™ water to sterilize the uterus.

Under clean-room conditions using sterile, large tissue grip forceps and large scissors, and wearing sterile gloves, mask, hood and gown, the entire length of the uterus on the surface opposite the major blood vessels is opened. Care is taken not to touch or damage the amniotic membranes of the fetus. Instruments that come in contact with the outer surface of the uterus are washed with 70% ethyl alcohol and sterilized with a Bunsen burner. Each fetus is gently lifted from the uterus and the umbilicus is cut at least 2 cm from the fetus. The still mainly frozen fetus is placed into a stainless steel pan.

With sterile gloves, the amniotic membrane is removed and the fetus transferred to a sterile glass dish. With a sterile scalpel, such as a #11 blade, the skin around each foot is sliced to make a circular incision. A single incision is made through the skin from the first cut, along the inner surface of each limb to the midline of the ventral surface of the trunk. A midline incision is made along the ventral surface of the trunk from the tail to the neck, taking care not to penetrate the underlying muscle tissue. A skin deep circular incision is made around the circumference of the head. The body skin is peeled off. The peeled skin is placed into a sterile container (one liter centrifuge bottle with cap) on ice.

The skins are combined with an equal volume of sterile ice, and the ground tissue is washed twice in 20 liters of ice cold 0.33×phosphate buffered saline (PBS):Mill-Q™ water (1:2) with about 30 minutes allowed for tissue to settle between washes. The tissue is evenly divided into one liter centrifuge bottles as required and each filled with 0.5M acetic acid and 4 mM EDTA. The centrifuge bottles are placed on a roller bottle apparatus for about seven days at a temperature of about 4° C.

On the eighth day after the beginning of the skin preparation, the centrifuge bottles are spun for thirty minutes at 5,000 rpm. The supernatant is aseptically collected in a sterile carboy (20 or 50 liters). The collected supernatant is filtered through four layers of sterile cheese cloth. Sterile sodium chloride is added to bring the solution to about 0.9M. It is stirred over a period of about one hour then placed in a cold room at about 4° C. overnight. The collagen is resuspended. The entire salt precipitated solution and the precipitate is dispensed into sterile one liter centrifuge bottles. The bottles are centrifuged at 5,000 rpm for about thirty minutes using a 6×one liter rotor at about 7,280 gs. The supernatant is removed, and the pellet is kept. To the pellet in each centrifuge bottle, 0.5M acetic acid pH 2.5 plus 4 mM EDTA is added. The pellets are dispersed in the medium and shaken in a gyrator shaker for about sixteen hours at a temperature of about 4° C. The pellets from the bottles are transferred to a six liter flask, by rinsing each bottle with the 0.5M acetic acid, EDTA solution and pouring the mix into the flask. In the six liter flask, the pellets are dispersed with a sterile glass rod. The flask is placed on a shaker for 24 hours at a temperature of about 4° C. The flask is checked for degree of solubilization and resuspension. More 0.5M acetic acid and EDTA solution may be added to bring the volume to five liters.

Sterile sodium chloride is added to the flask to bring the solution to about 0.7M. It is stirred periodically over a period of one hour and then placed in a cold room at a temperature of about 4° C. overnight allowing the salt to precipitate.

The contents are shaken and dispensed into one-liter sterile centrifuge bottles and spun at about 5,000 rpm for 30 minutes at 7,280 gs. A second resuspension is conducted with the step similar to the steps described above for the first resuspension. Instead, of resuspending in six liters, a total volume of two liters is employed in the resuspension process. The flask is shaken in the cold room overnight and its volume adjusted as necessary.

The solution is dialyzed three times for about 20–24 hours against one hundred liters of ice cold 0.05% 0.5M acetic acid in the cold room (4° C. ) using 6,000–8,000 MW cutoff, Spectrapore dialysis bags. The dialysis bag is slit with a sterile scalpel blade and the contents transferred into sterile 250 ml centrifuge bottles. The bottles are centrifuged at a temperature of about 4° C. at 10,000 rpm (13,000 g) for one hour. The supernatant is collected and stored in a sterile, sealed bottle.

A 0.5 ml aliquot of the supernatant is removed, combined with equal volume of concentrated hydrogen chloride and the collagen concentration measured using an hydroxyproline assay. The collagen is concentrated to a theoretical concentration of 5 mg/ml using a hollow fiber filter. The concentration can be confirmed with a hydroxyproline assay.

Liquid collagen is extracted from a suitable source, such as described above, and can be mixed with acetic acid and concentrated to five milligrams per milliliter. Liquid collagen can have an additive, such as alginate, or not have additives included. Liquid collagen is centrifuged at about 3,200 rpm and about 1,610 g to reduce gas dissolved in the liquid.

The liquid collagen is transferred into the reservoir chamber and further degassed by the application of a vacuum for a period of time, such as twenty minutes, thereby allowing essentially all the gas to be removed from the collagen. The liquid collagen is maintained in collagen reservoir chamber 10 at a temperature in the range of between about 4° C. and 22° C. Liquid collagen is pumped from collagen reservoir chamber 10 by infusion pump 14 through collagen reservoir tube 12 and extruded through spinneret nozzle 17 of spinneret 16. Various types of fibers can be formed depending upon the spinneret used. The bore holes in spinneret 16 can have various diameters, length to diameter ratios and tapered profiles to form fibers of different sizes and tensile strengths. The formed fibers can have sizes in the range of between 50 and 200 denier. The extruded collagen gel fiber 22 is directed into coagulation solution of coagulation bath 18 at a speed of about two milliliters per minute, for example.

Concurrently, coagulating solution 20 is circulated by circulation pump 28 in a direction parallel with the direction of the extruded collagen gel fiber 22. The speed of coagulating solution 20 can be the same as the speed of collagen gel fiber 22. In one embodiment, coagulating solution 20 is heated to a temperature of about 35° C., and the bath is monitored for pH, temperature and velocity. The pH is maintained in a range of between about eight and ten. Continuous collagen gel fiber 22 is formed by polymerization when the acid in the collagen is neutralized upon contact with the alkaline alginic acid/boric acid bath or other suitable neutralizing solution. The ratio of the coagulating bath speed to the infusion rate determines the size fiber for a given spinneret bore. During the residence of collagen fiber gel 22 in coagulation bath 18, polymerization and dehydration and occur. Fiber residence time is determined by the length of coagulating bath 18 and velocity of coagulation solution 20, the velocity of the collagen at spinneret 16 and the velocity at which the fiber is withdrawn from the bath. An example of a suitable residence time is about two minutes.

Another suitable solution for coagulating solution is an aqueous mixture of 0.85% methyl cellulose (4,000 centipoise), 0.31% boric acid and 0.375% glycine that is dispersed and dissolved. The mixture is chilled overnight to ensure that the components are dissolved. The next day, the bath is stirred and the pH is adjusted to a range of between about 10.2 and 10.5 with 10M sodium hydroxide. The mixture is filtered to remove particulates and microbial contaminants and is transferred to the coagulation bath 18. The mixture is heated to about 35° C., maintained at that temperature and circulated by pump 18. Fiber is formed by extrusion of collagen from spinneret 16 into coagulation bath 18.

At the end of coagulation bath 18, collagen gel fiber 22 is removed from coagulation solution 20. In one embodiment, a leader thread is tied to collagen gel fiber 22 to guide it to dehydrating bath 34. In the shown embodiment, collagen gel fiber 22 is directed over roller 32 after collagen gel fiber 22 exits from coagulation solution 20. The leader thread is carried along the downstream fiber process path and motorized rollers are activated to wind the thread which tows the collagen fiber.

Collagen gel fiber 22 is directed from roller 32 into dehydrating solution 36 in dehydrating bath 34 pulled by the leader thread. Dehydrating solution 36 is composed of about ninety percent ethanol and ten percent water. The ethanol further dehydrates and anneals the fiber and promotes the polymerization of the collagen to improve fiber strength. As done with coagulation solution 20, dehydrating solution 36 is recirculated by circulating pump 40 through recirculation loop 38 and dehydrating bath 34. Partially dehydrated fiber 44 can be passed through the dehydrating solution 36 one or more times. The fiber residence time in the dehydrating bath is determined by the speed of the fiber into and out of the bath, the distances between return rollers and the number of passes the fiber makes between return rollers. In one embodiment, the partly dehydrated fiber is in the dehydrating solution 36 for about five to six minutes. The partially dehydrated fiber 44 is directed from the dehydrating bath to particulate applicator 48. The surface of the partly dehydrated fiber 44 is sufficiently wet to permit adhesion to it of microparticulates, such as ADMAT or other particulate materials that can be applied as the next step of the process to produce a coated fiber.

Fiber 44 is directed through first opening 53 of particulate applicator 48 through horizontal tube 52 and out of second opening 55. Fiber 44 is positioned within tube 52 so that fiber 44 does not come into contact with any of the sides of tube 52.

In lower portion 58 of tube 52, microparticulate reservoir 56 is formed having been loaded with tissue specific microparticulates, for example, from alveolar bone which surrounds teeth. In one embodiment, the microparticulates have a diameter in the range of between about 10 and 500 micrometers. The reservoir can be cooled to protect the biological activity of the microparticulates. Energy is applied to microparticulate reservoir 56 to cause at least a portion of microparticulates to become airborne. In one embodiment, vibrational energy is directed into microparticulate reservoir. The vibrator operates between about 1,000–3,000 cycles/minutes at an amplitude sufficient to maintain a microparticulate cloud with no displacement of the fiber passing through it. The amount of microparticulate coating is controlled by the microparticulate size, total volume of microparticulates within the applicator chamber, dimensions of the applicator chamber, velocity of a fiber through applicator chamber, the free liquid content of the surface of the fiber, moisture content of the fiber, frequency of the applicator chamber vibration, amplitude of the applicator chamber vibration and static charge of the particles. Tube 52 is vibrated by a mechanical shaking mechanism capable of producing the required horizontal and vertical components of vibration. The vibrational generator excites the microparticulates into motion to produce a dust cloud.

Particulate applicator 48 can be operated intermittently as the fiber passes through the tube 52 to produce alternatingly coated and uncoated sections of dehydrated fiber 44. Other selected fiber coatings and other patterns can be applied. Microparticulates which become airborne and do not adhere to the fiber within tube fall under the gravity and return to lower portion 58 in microparticulate reservoir 56 either directly or by sliding down tube 52. In this manner, microparticulates are recycled back into microparticulate dust cloud 59 within tube 52.

Coated fiber 61 is directed from second applicator roller 50 of particulate 48 applicator to stretching roller means 62. Coated fiber is stretched by force developed between two groups of stretching rollers 64 rotating at slightly different rates of speed. The speeds of rotation of the roller groups 64 can be controlled with digital microprocessors arranged in a closed feedback loop. Stretching roller 64 speeds are controlled so that the ratio may be adjusted such that the fiber is stretched beyond the elastic yield point to produce a longer coated fiber of reduced diameter. Coated fiber 61 is wrapped three or four times around each set of stretching roller 64 to prevent slippage. Stretching rollers 64 can be arranged in series to stretch coated fiber 61 at each roller.

Stretched fiber 70 is directed from stretching roller means 62 to drying cabinet 68. Stretched fiber 70 is directed through opening 73 to drying cabinet 68 as drying cabinet 68 is flushed with warm dry filtered air at a temperature in the range of between about 35° C. and 39° C. Stretched fiber 70 is directed around drying cabinet rollers 74 contained in the drying cabinet 68 as air is blown over stretched fiber 70. Stretched fiber 70 maintains a minimum residence time to allow stretched fiber 70 to become dried. Drying cabinet rollers 74 are synchronized with the last group of stretching roller means 62 so that stretched fiber 70 does not stretch to a point of breaking.

Dried fiber 78 is directed through exit 75 of drying cabinet to take-up winder 76. Take-up winder 76 spools dried fiber 78 on a removable spindle bobbin. Take-up winder 76 incorporates the change of speed of dried fiber 78 as it is taken up on take-up winder 76 to provide a constant fiber line tension as the spool fiber package builds up radially. The fiber is wound either in order or randomly with the take-up mechanism.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A method for forming a collagen fiber having a microparticulate coating, said method comprising the steps of:

extruding collagen into a coagulation bath containing a coagulation solution, thereby forming at least a partially hydrated collagen fiber;

immersing said partially hydrated collagen fiber in a dehydrating solution contained in a dehydrating bath, thereby forming at least a partially dehydrated collagen fiber;

suspending microparticulates in a fluid medium, thereby forming a microparticulate suspension; and passing said partially dehydrated collagen fiber through said microparticulate suspension, thereby forming a microparticulate coating on said partially dehydrated collagen fiber.

2. The method of claim 1 wherein said extruding step comprises the steps of pressurizing said collagen with a positive displacement infusion pump; and passing said collagen through a spinneret having at least one bore.

3. The method of claim 2 further comprising the step of selecting said at least one bore to have a diameter between 100 microns and 1000 microns.

4. The method of claim 1 further comprising the step of flowing said coagulating solution in the direction along which said collagen is extruded.

5. The method of claim 1 further comprising the step of selecting said coagulation solution to include about 0.75% by weight of alkaline alginic acid in a boric acid buffer.

6. The method of claim 1 further comprising the step of selecting said coagulation solution to include about 0.85% by weight of methyl cellulose in a boric acid buffer.

7. The method of claim 1 further comprising the step of selecting said dehydrating solution to include a solution of 90% by weight of ethanol.

8. The method of claim 1 further comprising the step of selecting said dehydrating solution to include a solution of 90% by weight of acetone.

9. The method of claim 1 wherein said suspending step further comprises the step of selectively vibrating a tube section containing fluid and microparticulates.

10. The method of claim 9 wherein said tube section is a bent tube section.

11. The method of claim 10 further comprising the step of forming said bent tube section at an angle chosen to permit a fiber to pass through said tube section without contacting said tube section.

12. The method of claim 11 further comprising the step of selecting said bent tube section to have a diameter of approximately 1.8 centimeters, a length of approximately seventeen centimeters, and a bend of approximately fifteen degrees.

13. The method of claim 9 wherein said step of vibrating said tube section further comprises the step of selectively vibrating said tube section in a direction orthogonal to the plane containing the longitudinal axis of said tube section.

14. The method of claim 9 wherein said step of vibrating said tube section further comprises the step of selectively vibrating said tube section in a direction coplanar with the plane containing the longitudinal axis of said tube section.

15. The method of claim 9 wherein said step of vibrating said tube section further comprises the step of controlling the frequency of vibration.

16. The method of claim 15 further comprising the step of selecting the frequency of vibration to be between 1000 and 3000 cycles per minute.

17. The method of claim 9 wherein said step of vibrating said tube section further comprises the step of controlling the amplitude of vibration.

18. The method of claim 17 further comprising the step of selecting the amplitude of vibration to be one millimeter or less.

19. The method of claim 1 further comprising the step of stretching said partially dehydrated collagen fiber by securely winding a first section of said partially dehydrated collagen fiber around a first roller having a first rotational frequency and securely winding a second section of said partially dehydrated collagen fiber around a second roller having a second rotational frequency greater than said first rotational frequency.

20. The method of claim 1 further comprising the step of drying said partially dehydrated collagen fiber.

21. The method of claim 20 wherein the drying step further comprises the step of exposing said fiber to a dehydrating gas.

22. The method of claim 21 further comprising the step of selecting said dehydrating gas to be a dry nitrogen gas.

23. The method of claim 20 further comprising the step of disposing said dehydrating gas at a temperature between 35° C. and 39° C. and at a relative humidity between 10% and 20%.

24. The method of claim 1 further comprising the step of providing said microparticulates between 10 and 500 micrometers in diameter.

25. The method of claim 1 wherein said microparticulates are formed from animal tissue.

26. The method of claim 25 wherein said animal tissue is selected from a group consisting of porcine animals, bovine animals, ovine animals, and marine animals.

* * * * *